US00PP31288P3

(12) United States Plant Patent
Park et al.

(10) Patent No.: US PP31,288 P3
(45) Date of Patent: Dec. 31, 2019

(54) ***CITRUS RETICULATA* BLANCO PLANT NAMED 'TAMDORI'**

(50) Latin Name: ***Citrus reticulata* Blanco**
Varietal Denomination: Tamdori

(71) Applicant: THE RURAL DEVELOPMENT ADMINISTRATION, REPUBLIC OF KOREA, Chungcheongnam-do (KR)

(72) Inventors: Jaeho Park, Seogwipo-si (KR); Sangwoog Koh, Seogwipo-si (KR); Sukman Park, Seogwipo-si (KR); Minju Kim, Seogwipo-si (KR); Yonghun Choi, Seogwipo-si (KR); Su-Hyun Yun, Seogwipo-si (KR); I-Ung Yang, Seogwipo-si (KR)

( * ) Notice: Subject to any disclaimer, the term of this patent is extended or adjusted under 35 U.S.C. 154(b) by 0 days.

(21) Appl. No.: 14/756,933

(22) Filed: Oct. 30, 2015

(65) Prior Publication Data

US 2017/0127586 P1 May 4, 2017

(51) Int. Cl.
*A01H 5/08* (2018.01)
*A01H 6/78* (2018.01)

(52) U.S. Cl.
USPC ..... Plt./201

(58) Field of Classification Search
USPC ..... Plt./156, 201
See application file for complete search history.

(56) References Cited

PUBLICATIONS

Korea Seed & Variety Service website—citation for application No. 2014-335. http://www.seed.go.kr/english/function/system_05_view.jsp?appl_idty=110435. Accessed May 1, 2017. 1 page.*

* cited by examiner

*Primary Examiner* — Susan McCormick Ewoldt
*Assistant Examiner* — Karen M Redden
(74) *Attorney, Agent, or Firm* — Baker Donelson

(57) ABSTRACT

A new and distinct *Citrus reticulate* Blanco plant named 'Tamdori', characterized by its upright plant type and strong vigor, fertile but self-incompatibility pollen, orange fruit color, germination stage in middle of April, blooming state in late May, fruits start coloring in late October and finish coloring in late December, mature stage in middle of February, fruit weight at about 168.9 g, fruit skin thickness at about 2.3 mm and easy to peel, fruit flesh rate at about 79.9%.

1 Drawing Sheet

Latin name of the genus and species of the plant claimed: *Citrus reticulata* Blanco.

Variety denomination: 'Tamdori'.

BACKGROUND OF THE INVENTION

The new and distinct cultivar is a product of a breeding program by the inventors by crossing a Japanese variety 'Kiyomi' (not patented) and an American variety 'Fortune' mandarin (as the pollen parent, not patented) in 2005. The seeds obtained by the cross were sowed in a greenhouse in the spring of 2006. The seedlings germinated from the seeds were upper-position grafted onto 'satsuma' mandarin in the spring of 2007. The plants started fruiting in 2011. In the same year, the first screening was carried out, and the one called 'Jegamna-40' was selected for good quality. In the last screening which carried out in 2013, 'Jegamna-40' was finally selected as the new variety and named 'Tamdori'.

After hybridization of the parents, the variety was asexually propagated by grafting onto 'Satsuma' root stock in Jeju-do, Korea for three generations and there was no genetic variation. The observed plant retains its distinctive characteristics and reproduces true to type in successive generations. Therefore, its traits are stable. The rootstock of 'Satsuma' is the tangerine tree, and tangerine has no patent status.

The fruit characteristics of 'Tamdori' are in the table below. The test carried out from 2011 to 2013.

TABLE 1

Fruit Characteristics

| Survey date (yy.mm.dd) | Fruit weight (g) | Flesh rate (%) | Fruit shape index | Thickness of the skin (mm) |
|---|---|---|---|---|
| 11.02.07 | 130.3 | 84.9 | 123 | 1.5 |
| 11.02.21 | 154.3 | 82.7 | 121 | 2.0 |
| 11.03.08 | 186.5 | 74.7 | 121 | 3.1 |
| 11.03.29 | 158.6 | 79.5 | 114 | 3.0 |
| 12.01.05 | 124.0 | 87.0 | 139 | 1.2 |
| 12.01.20 | 144.0 | 85.7 | 135 | 1.6 |
| 12.02.06 | 147.4 | 84.8 | 145 | 1.7 |
| 12.02.20 | 135.2 | 84.0 | 128 | 1.5 |
| 13.01.22 | 175.3 | 84.6 | 116 | 2.1 |
| 13.02.12 | 168.9 | 79.9 | 108 | 2.3 |
| 13.02.25 | 170.1 | 79.5 | 114 | 2.4 |

| Survey date (yy.mm.dd) | Seed grain number | Sugar (°Bx) | Acidity (%) | Sugar acid ratio |
|---|---|---|---|---|
| 11.02.07 | 0.0 | 14.4 | 1.34 | 10.71 |
| 11.02.21 | 6.8 | 14.9 | 1.04 | 15.24 |
| 11.03.08 | 3.6 | 14.9 | 0.87 | 17.74 |
| 11.03.29 | 1.5 | 16.1 | 0.78 | 20.85 |
| 12.01.05 | 5.0 | 13.1 | 1.14 | 11.55 |

TABLE 1-continued

| Fruit Characteristics | | | | |
|---|---|---|---|---|
| 12.01.20 | 0.8 | 13.9 | 0.99 | 14.31 |
| 12.02.06 | 3.8 | 13.5 | 0.81 | 16.64 |
| 12.02.20 | 8.8 | 15.1 | 0.65 | 23.13 |
| 13.01.22 | 11.8 | 13.9 | 1.19 | 11.68 |
| 13.02.12 | 10.8 | 14.6 | 1.17 | 12.46 |
| 13.02.25 | 13.8 | 14.9 | 0.83 | 18.09 |

Fruit shape index = The transverse diameter ÷ The longitudinal diameter × 100

SUMMARY OF THE INVENTION

The cultivar 'Tamdori' has not been observed under every possible environmental conditions. Therefore, the may be variations in the phenotype due to varying environmental conditions such as temperature, day length and light intensity. However, the genotype will not vary.

The following traits have been repeatedly observed and are determined to be the characteristics of the new cultivar of *Citrus reticulata* Blanco. These attributes in combination distinguish 'Tamdori' as unique from and all other varieties of *Citrus reticulata* Blanco known to Inventors.

1. The plant type of 'Tamdori' is upright and the tree vigor is strong.
2. 'Tamdori' has fertile pollen but it is self-incompatibility.
3. The fruit color is orange.
4. Germination stage of 'Tamdori' is in the middle of April, and the blooming stage is in late May.
5. Fruits start coloring in late October and finish coloring in late December.
6. The mature stage is in the middle of February.
7. Fruit weight is about 168.9 g.
8. Fruit skin thickness is about 2.3 mm so it is easy to peel.
9. The fruit flesh rate is about 79.9%.
10. 'Tandori' is self-compatible, but when fertilized by other variety, several seeds can be gained.
11. Sugar of fruit juice is about 14.6 ° Bx, and the sugar acid ratio is about 12.46.
12. 'Tamdori' has small leaf, the leaf area is about 27.9 $cm^2$. The leaf length is about 9.9 cm, and the leaf width is about 4.3 cm.
13. The length of leaf petiole is about 19.2 mm and the thickness is about 1.0 mm.

Plants of the new cultivar 'Tamdori' are similar to plants of the seed parent 'Kiyomi' in most horticultural characteristics, however, the plants of the new cultivar 'Tamdori' produce fruit that are less acidic than the parent. Compared to the parent, 'Tamdori' produces fruit with skin thickness of 2.3 mm. Fruit of 'Tamdori' has a considerable number of seeds.

The new cultivar differs from the closest comparable plants as follows:

TABLE 2

| Comparison With Closest Variety | | | |
|---|---|---|---|
| Denomination | Characteristic in which the | The expression of the characteristic | |
| of similar variety | similar variety is different | Similar variety | Candidate variety |
| Kiyomi | Plant: type | medium | upright |
| | Plant: tree vigor | medium | strong |
| | Flower: the pollen | no pollen | May have fertile pollen |

TABLE 2-continued

| Comparison With Closest Variety | | | |
|---|---|---|---|
| Denomination | Characteristic in which the | The expression of the characteristic | |
| of similar variety | similar variety is different | Similar variety | Candidate variety |
| | Fruit: weight | 291.6 g | 168.9 g |
| | Fruit: flesh rate | 72.6% | 79.9% |
| | Fruit: skin thickness | 4.6 mm | 2.3 mm |
| | Fruit: number of seeds | 0.0 | 10.8 |
| | Fruit juice: Sugar (°Bx) | 11.0 | 14.6 |
| | Fruit: sugar acid ratio | 9.43 | 12.46 |
| | Fruit: color | yellowish orange | medium orange |
| | Leaf: leaf area | about 72.8 $cm^2$ | about 27.9 $cm^2$ |
| | Leaf: leaf length | 15.5 cm | 9.9 cm |
| | Leaf: leaf width | 6.9 cm | 4.3 cm |
| | Leaf petiole: length | 23.1 mm | 19.2 mm |
| | Leaf petiole: thickness | 1.7 mm | 1.0 mm |
| | Mature stage | early (in the middle of March) | very early (in the middle of February) |

TABLE 3

| Comparison between 'Tamdori' and 'Fortune' | | |
|---|---|---|
| Characteristic(s) in which your candidate variety differs from the similar variety(ies) | Describe the expression of the characteristic(s) for your candidate variety 'Tamdori' | Describe the expression of the characteristic(s) for the similar variety 'Fortune' |
| Plant: Type | upright | spreading |
| Flower: activity pollen | absent | present |
| Leaf: leaf area | 27.9 cm2 | 25.0 cm2 |
| Flower: length | 15.2 | 15.3 mm |
| Flower: width | 6.1 | 6.2 mm |
| Fruit: length | 65.6 mm | 49.4 mm |
| Fruit: width | 70.7 mm | 61.9 mm |
| Fruit juice: total soluble solids | 14.6 | 13.6 |
| Fruit juice: acid | 1.17 | 2.1 |
| Fruit: number of seeds | 5.6 | 12.5 |
| Mature stage | Mid-late(mid-February) | Late(mid-March) |
| Parthenocarpy | present | absent |
| Plant Self Incompatibility | present | absent |
| Tree vigor | strong | middle |

BRIEF DESCRIPTION OF THE DRAWINGS

The accompanying colored photographs illustrate the overall appearance and distinct characteristics of the new *Citrus reticulata* Blanco 'Tamdori' showing colors as true as is reasonably possible with colored reproduction of this type. These photos were taken in 2013 in Korea. Colors in the photographs may differ slightly from the color values cited in the detailed botanical description which accurately describes the color of the 'Tamdori'.

DETAILED BOTANICAL DESCRIPTION

Figure 1:
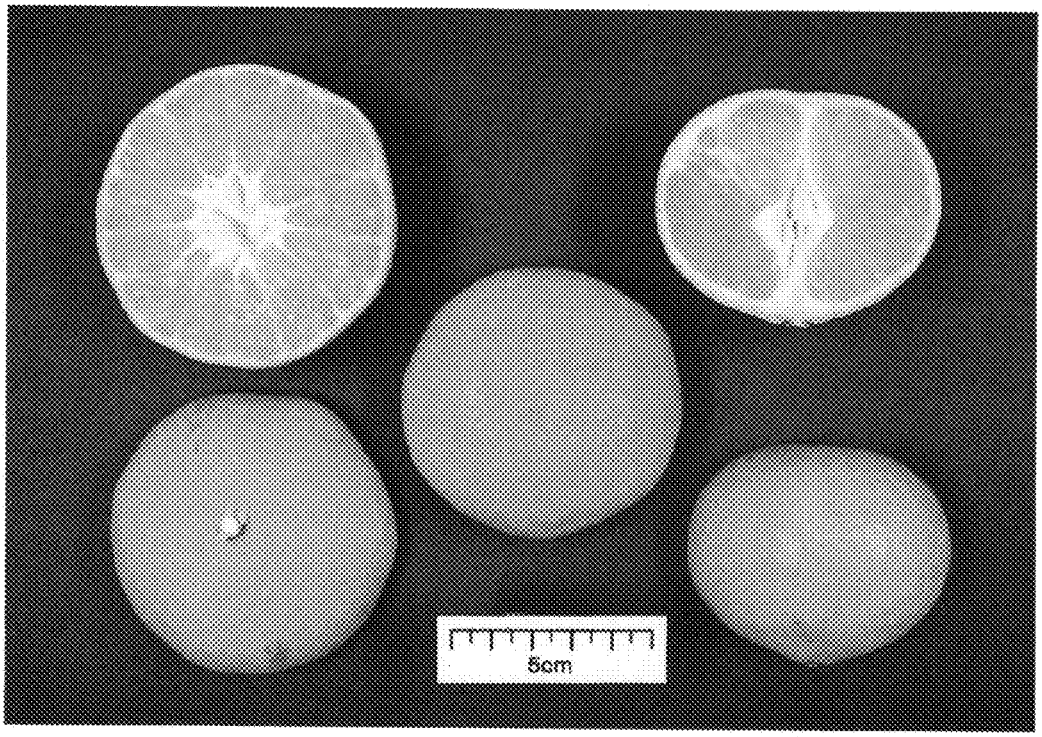
FIG. 1 provides multiple views of typical fruits harvested from 'Tamdori' of a four years old tree. Top, bottom and side views of the whole, unpeeled fruit is shown as well as two cross-sectional views of the inside of the fruit.
Figure 2:
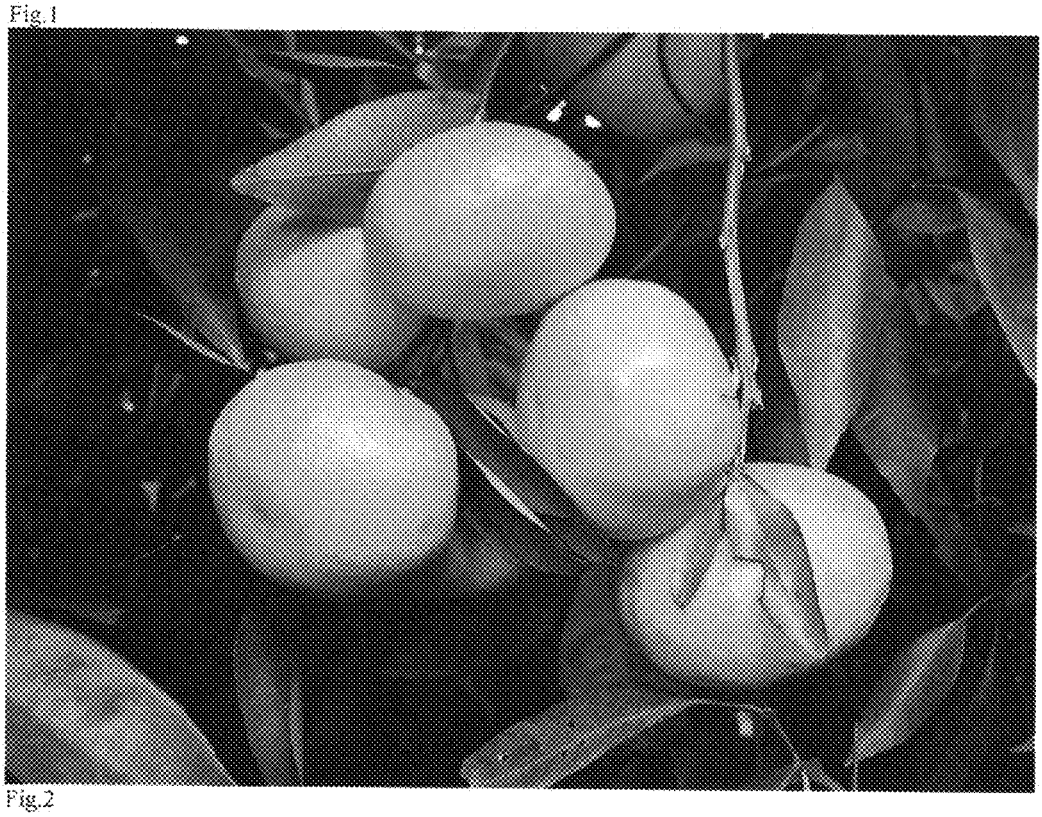
FIG. 2 illustrates in full color typical foliage and fruits of 'Tamdori' on a four years old tree.

The following is a detailed description of the new cultivar 'Tamdori' plants as grown in Korea. The descriptors were taken between 2011 and 2013.

The chart used in the identification of colors described herein is The R.H.S. Colour Chart of The Royal Horticultural Society, 2007, Fifth edition, except where general color terms of ordinary significance are used.

TABLE 4

Color of 'Tamdori' and 'Kiyomi'

| | Tamdori | | Kiyomi | |
|---|---|---|---|---|
| | COLOR | | COLOR | |
| Fruit: surface color | medium orange | RHS orange 30D | yellowish orange | RHS orange 26B |
| Fruit: flesh color | Light orange | RHS orange 24A | | |
| leaf: upper surface color of young leaves | Green | RHS green 137A | | |
| leaf: lower surface color of young leaves | Green | RHS green 138A | | |
| Leaf: upper surface color of mature leaves | Green | RHS green 137A | | |
| Leaf: lower surface color of mature leaves | Green | RHS green 137A | | |
| Stem: bark color | Yellow-green | RHS yellow-green 148A | | |
| Flower: anther color | Light yellow | RHS Yellow-Orange 15C | | |
| Flower: color of opened flower | White | RHS NN 155 White C | | |
| Petal: upper surface color | White | RHS NN 155 White C | | |
| Petal: lower surface color | White | RHS NN 155 White C | | |
| Seed: seed color | No Seed | | | |

Botanical classification: *Citrus reticulata* Blanco 'Tamdori'.

Propagation: 'Tamdori' is typically grafted onto rootstock of 'Satsuma' mandarin.

Plant:

*Age of the plant described.*—Approximately six years.
*Chromosome multiples.*—2.
*Plant posture.*—Upright.
*Plant density of spines.*—None or sparse.
*Height.*—2 m.
*Width.*—1.6 m.
*Shape.*—Upright.
*Root system.*—Taproot.

Foliage:

*Leaf color.*—Green.
*Leaf area.*—27.9 $cm^2$.
*Leaf length.*—9.9 cm.
*Leaf width.*—4.3 cm.
*Shape in cross section.*—Intermediate.
*Blistering.*—Absent.
*Undulation of margin.*—Week.
*Incisions of margin.*—Crenate.
*Shape of apex.*—Acute.
*Leaf length/width ratio.*—2.29.
*Leaf petiole length.*—23.1 mm.
*Leaf petiole thickness.*—1.0 mm.
*Presence of wings.*—Absent.
*Leaf arrangement.*—Alternate.
*Venation pattern.*—Pinnate.
*Leaf margins.*—Crenate.
*Texture of leaf.*—Smooth.
*Length and color of stipules, if present.*—Absent.

Flower:

*Flower calyx diameter.*—3.6 mm.
*Flower petal length.*—15.2 mm.
*Flower petal width.*—6.1 mm.
*Flower petal length/width ratio.*—2.5.
*Flower stamen length.*—8.0 mm.
*Flower anther color.*—Light yellow.
*Flower.*—Pollen absent.
*Flower diameter.*—About 2.0 cm to about 2.5 cm when fully opened.
*Petal length.*—About 15.2 mm.
*Petal width.*—About 6.1 mm.
*Petal texture and margin.*—Smooth.
*Fragrance flower.*—Absent.
*Bud shape.*—Elongated cone.
*Bud size.*—About 6 mm to about 9 mm in diameter.
*Average number of flowers per panicle.*—No panicle in this cultivar.
*Style length.*—About 14.4 mm to about 16.7 mm.
*Ovary shape.*—Short oval.
*Stamen number.*—About 16 to about 20, with complete style development.
*Stamen length.*—About 7.0 mm to about 9.3 mm.
*Anther color.*—Light yellow (RHS Yellow-Orange 15C).
*Pedicle length.*—1.1 cm.
*Pedicule color.*—RHS Yellow-Green Group 144M. In Jeju-do, Korea, the time for the first bloom is approximately March 15th, the end of bloom is approximately April 20th.

Fruit:

*Fruit weight.*—168.9 g.
*Fruit length.*—65.6 mm.
*Fruit width.*—70.7 mm.
*Fruit length/width ratio.*—0.93.
*Fruit neck.*—Absent.
*Fruit areola.*—Absent.
*Fruit surface color.*—Medium orange.
*Fruit surface roughness.*—Rough.
*Fruit fresh color.*—Light orange.
*Fruit skin thickness.*—2.3 mm.
*Fruit skin strength.*—Medium.
*Fruit flesh rate.*—79.9%.
*Fruit number of seeds.*—10.8.
*Fruit sugar acid ratio.*—12.46.
*Fruit juice total soluble solids.*—14.6° Bx.
*Fruit juice acidity.*—1.17.
*Mature stage.*—Very early.
*Parthenocarpy.*—Present.
*Self-incompatibility.*—Present.
*Tree vigor.*—Strong.
*Pollinator.*—Not required.
*Parthenocarpy trait.*—Present.

*Productivity of fruit.*—About 2500 kg/10 acre to about 3000 kg/10 acre.

*Market use of the fruit of the observed plant.*—Fresh fruit.

*Other fruit features.*—'Tamdori' is intermediate resistant to *citrus* scab disease, *citrus* canker and melanose. For the very early mature stage, 'Tamdori' should be protected when cultured. Since the fruit would be matured in mid-February of the second year, and the cold season may reduce the quality of the fruit if the fruit is planted in open field, 'Tamdori' needs to be planted under protected environment. Pruning on 'Tamdori' is the same as other variety which belongs to *Citrus reticulata* Blanco. Fruit and plant are damaged when the temperature is below −7° C.

Table 5. Descriptive comparison between 'Tamdori' and another known *Citrus reticulate* cultivar 'Setoka' (not patented).

TABLE 5

Descriptive comparison between 'Tamdori' and another known *Citrus reticulate* cultivar 'Setoka' (not patented).

| Variety Denomination | Harvest time | Shape Index | Sugar degree ("BX) | Acidity/ % | Fruit weight/g |
|---|---|---|---|---|---|
| Setoka | Early-Late February | 129.6 | 13 | 1.0 | 200 |
| Tamdori | Mid-late February | 108 | 14.6 | 1.17 | 168.9 |

Table 6. Characteristic and observed dates of first and last pick in the specified location of culture as observed in Jeju-do, Korea.

TABLE 6

Characteristic and observed dates of first and last pick in the specified location of culture as observed in Jeju-do, Korea.

| Time | Fruit weight/g | Flesh rate/% | Shape Index | Pericap thickness/ mm |
|---|---|---|---|---|
| 11.02.07 | 130.3 | 84.9 | 123 | 1.5 |
| 11.02.21 | 154.3 | 82.7 | 121 | 2.0 |
| 11.03.08 | 186.5 | 74.7 | 121 | 3.1 |
| 11.03.29 | 158.6 | 79.5 | 114 | 3.0 |
| 12.01.05 | 124.0 | 87.0 | 139 | 1.2 |
| 12.01.20 | 144.0 | 85.7 | 135 | 1.6 |
| 12.02.06 | 147.4 | 84.8 | 145 | 1.7 |
| 12.02.20 | 135.2 | 84.0 | 128 | 1.5 |
| 13.01.22 | 175.3 | 84.6 | 116 | 2.1 |
| 13.02.12 | 168.9 | 79.9 | 108 | 2.3 |
| 13.02.25 | 170.1 | 79.5 | 114 | 2.4 |

| Time | Seed number | Sugar degree ("Bx) | Acidity/ % | Acid-sugar ratio |
|---|---|---|---|---|
| 11.02.07 | 0.0 | 14.4 | 1.34 | 10.71 |
| 11.02.21 | 6.8 | 14.9 | 1.04 | 15.24 |
| 11.03.08 | 3.6 | 14.9 | 0.87 | 17.74 |
| 11.03.29 | 1.5 | 16.1 | 0.78 | 20.85 |
| 12.01.05 | 5.0 | 13.1 | 1.14 | 11.55 |
| 12.01.20 | 0.8 | 13.9 | 0.99 | 14.31 |
| 12.02.06 | 3.8 | 13.5 | 0.81 | 16.64 |
| 12.02.20 | 8.8 | 15.1 | 0.65 | 23.13 |
| 13.01.22 | 11.8 | 13.9 | 1.19 | 11.68 |
| 13.02.12 | 10.8 | 14.6 | 1.17 | 12.46 |
| 13.02.25 | 13.8 | 14.9 | 0.83 | 18.09 |

Regarding the observed plant's drought/heat tolerance, although the variety has not been tested for drought and heat resistance, it can grow at a temperature of about 40° C., and without irrigation for about 45 days does not have much effect on the growth of the variety.

The invention claimed is:

1. A new and distinct cultivar of *Citrus reticulate* Blanco plant named 'Tamdori' as herein illustrated and described.

* * * * *